United States Patent [19]

Burckhardt et al.

[11] 4,042,703
[45] Aug. 16, 1977

[54] METHOD OF TREATING AND PREVENTING COCCIDIOSIS

[75] Inventors: Urs Burckhardt; Alfred Meyer, both of Basel, Switzerland

[73] Assignee: Ciba-Geigy Corporation, Ardsley, N.Y.

[21] Appl. No.: 646,315

[22] Filed: Jan. 2, 1976

[30] Foreign Application Priority Data

Jan. 8, 1975 Switzerland .......................... 167/75
Nov. 27, 1975 Switzerland ...................... 15389/75

[51] Int. Cl.² .......................................... A61K 31/415
[52] U.S. Cl. ................................................ 424/273 R
[58] Field of Search ........................................ 424/273

[56] References Cited
PUBLICATIONS

Trout et al. – Chem. Abst., vol. 66 (1967), p. 115,645u.

Primary Examiner—Sam Rosen
Attorney, Agent, or Firm—Frederick H. Rabin

[57] ABSTRACT

The present invention relates to new compositions, containing as active ingredient 4-nitro-5-carbamoyl-imidazole derivatives, which compositions are for the treatment and prevention of coccidiosis in poultry.

The 4-nitro-5-carbamoyl-imidazole derivatives correspond to the following general formula I

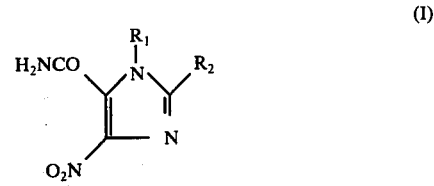

wherein $R_1$ and $R_2$ each independently represent hydrogen, or an alkyl radical having 1 to 4 carbon atoms.

2 Claims, No Drawings

METHOD OF TREATING AND PREVENTING COCCIDIOSIS

The present invention relates to new compositions, containing as active ingredient 4-nitro-5-carbamoylimidazole derivatives, which compositions are for the treatment and prevention of coccidiosis in poultry.

Among the diseases occurring in poultry, coccidiosis is the most prevalent. It is caused by protozoal parasites of the genus Eimeria, such as *Eimeria tenella, Eimeria brunetti, Eimeria maxima, Eimeria necatrix, Eimeria acervulina*, etc. . Birds infested by coccidia have a poor increase in weight, accompanied by bleeding in the intestines and discharge of blood in the excretions; in the case of severe infestation, coccidiosis results in a high level of mortality of the poultry. It is known of commercial coccidiostatically effective compounds that they lead within a short time to the development of resistance by the parasites. It is therefore of the utmost importance for poultry breeding that new compounds for the control and prevention of this disease be developed.

The 4-nitro-5-carbamoyl-imidazole derivatives correspond to the following general formula I

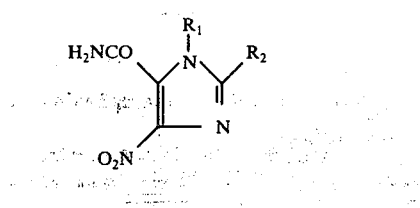

(I)

wherein $R_1$ and $R_2$ each independently represent hydrogen, or an alkyl radical having 1 to 4 carbon atoms.

The following compounds have proved particularly effective:
1-methyl-4-nitro-5-carbamoyl-imidazole
4-nitro-5-carbamoyl-imidazole,
1-ethyl-2-methyl-4-nitro-5-carbamoyl-imidazole.

In the compositions of the invention, the active ingredients are protected against premature decomposition by suitable protective formulations (e.g. coated granules), by incorporation into hydrophobic materials (e.g. paraffin, silicone oils or silicone waxes), or by absorption onto inert solid carriers such as kaolin, talcum, bentonite, kieselguhr or bolus alba. The compositions are administered to the animals preferably as a constituent of the feed; they can however also be administered with the drinking water.

If the compositions are in the form of feed concentrates, then the carriers used are, e.g., production feed, fodder grain or protein concentrates. Such feed concentrates or feeding stuffs may contain, in addition to the active ingredients, also additives, vitamines, antibiotics, chemotherapeutical agents or other pesticides, especially bacteriostatics, fungistatics, anthelmintics, coccidiostatics, also hormone preparations, substances having anabolic activity, or other substances promoting growth, affecting the quality of the meat of slaughter cattle, or being in some other way beneficial for the organism.

The finished feed contains the active ingredients at a concentration of 0.0025 to 0.05 percent by weight, preferably 0.01 to 0.04 percent by weight.

A feed mixture of this kind is described in the following. Percentages denote per cent by weight.

The active ingredient in an amount of 400 mg/kg is added, by mixing, to a commercial chicken feed. In order to ensure a good distribution, a 20% active-ingredient concentrate is firstly prepared in a mortar with the use of calcium carbonate or cellulose powder or pre-sieved chicken meal; this concentrate is then processed by the subsequent addition of sieved chicken meal into a premix containing 5% of active ingredient, and finally into a final feed mixture containing 0.04% of active ingredient, the composition of this feed mixture being as follows:

| feed mixture | |
|---|---|
| raw fibre | 4.5 % |
| raw protein | 18.5 % |
| digestible protein | 15.7 % |
| total nutritive substances | 66.5 % |
| vitamine A | 9000 I.U./kg |
| vitamine $D_3$ | 1200 I.U./kg |
| vitamine $B_2$ | 6 mg/kg |

The coccidiostatic action of the active ingredients of the formula I is demonstrated in the following test.

Tests on chickens infested with Eimeria tenella

Ten 8-day-old chickens are infected with 80,000 sporulated oocysts of Eimeria tenella. During 3 days before and 10 days after infestation, medicated chicken feed containing 400 ppm of active ingredient is administered ad libitum. At the end of the test period, the chickens are dissected. There are used as control groups in each case 10 uninfested, untreated chickens as well as 10 infested chickens. The absorbed active ingredient per group is determined by re-weighing the feed. Mortality, increase in weight, condition of the caeca as well as secretion of oocysts, compared with corresponding results obtained for the two control groups, are taken as parameters of effectiveness.

The active ingredients are tolerated asymptomatically (no mortality) by the chickens: no oocysts are secreted and no caecum lesions are observed.

In the case of the infested control birds, the mortality rate is 20%, and severe caeca lesions are observed.

In the two following independent tests a) and b) with Eimeria tenella, the excellent coccidiostatic effectiveness is illustrated by a comparison between 1-methyl-4-nitro-5-cyano-imidazole (known from the U.S. Pat. Spec. No. 2,974,087) and 1-methyl-4-nitro-5-carbamoyl-imidazole (according to the present invention).

Tests on chickens infested with Eimeria tenella

Ten 5-day-old chickens are infested with 100,000 sporulated oocysts of Eimeria tenella. During 3 days before infestation and during 10 days after infestation, medicated chicken feed containing 400 ppm of active ingredient is administered ad libitum. The chickens are dissected at the end of the test period. There are used as control groups in each case 10 uninfested, untreated chickens as well as 10 infested chickens. The absorbed amount of active ingredient per group is determined by re-weighing the feed. The effectiveness parameters used are mortality rate, weight increase as well as secretion of oocysts, compared with the corresponding results obtained with the two control groups.

| Effectiveness parameters | | * | | ** | | Uninfested control | | Infested control |
|---|---|---|---|---|---|---|---|---|
| mortality | a) | 1/10 | a) | 0/10 | a) | 0/10 | a) | 5/10 |
| | b) | 2/10 | b) | 0/10 | b) | 0/10 | b) | 3/10 |
| weight (g) (mean value) | a) | 1st day: 68.9 14th day: 96.4 | a) | 1st day: 68.0 14th day: 202.0 | a) | 1st day: 68.0 14th day: 214.6 | a) | 1st day: 68.0 14th day: 139.2 |
| | b) | 1st day: 57.4 14th day: 47.4 | b) | 1st day: 57.8 14th day: 161.6 | b) | 1st day: 57.7 14th day: 198.4 | b) | 1st day: 57.7 14th day: 146.7 |
| oocyst secretion | a) | virtually none | a) | none | a) | none | a) | severe |
| | b) | as a) | b) | none | b) | none | b) | severe |

\* 1-methyl-4-nitro-5-cyano-imidazole) known from US 2,974,087)
\*\* 1-methyl-4-nitro-5-carbamoyl-imidazole (of the invention)

This test shows that, compared with the carbamoyl-imidazole(\*\*) of the invention, the known cyano-imidazole (\*) causes a greatly reduced increase of weight or even a decrease of weight, associated with a higher rate of mortality.

The active ingredients of the formula I are in some cases new and in some cases already described. Thus, 1-methyl-4-nitro-5-carbamoyl-imidazole is known from Helv. Chim. Acta 7, 713-719 (1924); 4-nitro-5-carbamoyl-imidazole from Chem. Ber. 56, 683-685 (1923); and 1-ethyl-2-methyl-4-nitro-5-carbamoyl-imidazole from Anales Sec. Espanola Fisica Quim. 24, 731-737 (1926).

The active ingredients are producible by methods known per se, and can be obtained, for example, by processes described in the given publications.

We claim:

1. A method for the treatment and prevention of coccidiosis in poultry, which comprises feeding the poultry an effective amount of a compound of the formula:

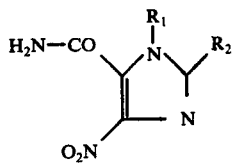

wherein each of $R_1$ and $R_2$ represents hydrogen or alkyl of from 1 to 4 carbon atoms.

2. A method according to claim 1 in which the compound is 1-methyl-4-nitro-5-carbamoyl-imidazole.